United States Patent

O'Neil

Patent Number: 5,865,176
Date of Patent: Feb. 2, 1999

[54] ARTIFICIAL AIRWAY DEVICE WITH SEALING CUFF FOR DISTAL END

[75] Inventor: Michael Jeffrey O'Neil, Hollybank Haughs Road, Quarmby, Huddersfield, W. Yorkshire HD3 4YS, England

[73] Assignees: Michael Jeffrey O'Neil; Biosil Limited, both of Great Britain

[21] Appl. No.: 913,020

[22] PCT Filed: Mar. 6, 1996

[86] PCT No.: PCT/GB96/00516

§ 371 Date: Nov. 4, 1997

§ 102(e) Date: Nov. 4, 1997

[87] PCT Pub. No.: WO96/27404

PCT Pub. Date: Sep. 12, 1996

[30] Foreign Application Priority Data

Mar. 8, 1995 [GB] United Kingdom ............. 9504657

[51] Int. Cl.[6] .............. A61M 16/00; A61M 29/00; A62B 9/06
[52] U.S. Cl. ............. 128/207.15; 128/207.14; 604/101
[58] Field of Search ........... 128/200.26, 207.14–207.16; 604/101

[56] References Cited

U.S. PATENT DOCUMENTS

| 3,874,377 | 4/1975  | Davidson        | 128/207.15 |
| 3,915,173 | 10/1975 | Brekke          | 128/207.15 |
| 4,166,468 | 9/1979  | Haynie          | 128/207.15 |
| 4,230,108 | 10/1980 | Young           | 128/207.15 |
| 4,256,099 | 3/1981  | Dryden          | 128/200.26 |
| 4,327,720 | 5/1982  | Bronson et al.  | 128/207.15 |
| 5,339,808 | 8/1994  | Don Michael     | 128/207.15 |

*Primary Examiner*—Kimberly L. Asher
*Attorney, Agent, or Firm*—Trexler, Bushnell, Giangiorgo & Blackstone, Ltd.

[57] ABSTRACT

An artificial airway device to facilitate the ventilation of the lungs of an unconscious patient and permitting access to the patient's oesophagus consists of a hollow tube which is left open at both ends having an aperture providing fluid communication between the interior and exterior of said tube disposed at a position between its ends. The tube is provided with an inflatable cuff on one side of the aperture for providing a seal in the patient's pharynx and an inflatable cuff at the end of the tube on the opposite side of the aperture to the inflatable cuff for providing a seal in the patient's oesophagus and also releasably closing the end of the tube.

25 Claims, 3 Drawing Sheets

ARTIFICIAL AIRWAY DEVICE WITH SEALING CUFF FOR DISTAL END

This invention relates to an artificial airway device to facilitate the ventilation of the lungs of an unconcious patient.

BACKGROUND

It is known to provide an artificial airway device in the form of a laryngeal mask comprising an airway tube opening into the interior space of a mask portion which is positioned in the hypopharynx of the patient and forms a seal around the inlet to the larynx to form an airway to the patients lungs permitting spontaneous or controlled ventilation thereof.

Such a known artificial airway device suffers from several disadvantages. As the mask portion has to provide a seal around the inlet to the patients larynx, it is necessary for the mask to be formed with a collar engaging in sealing contact with the tissues around the circumference of the patients laryngeal inlet, resulting in the need for the mask portion to be of a relatively large size and complex shape.

The complexity of the shape of the mask portion is further increased by the need to provide restraining means extending across the open space defined by the collar to reduce the risk of a blockage to the airway by the epiglottis falling inwards into said open space.

The size and complexity of shape of the mask portion of this known type of artificial airway device makes it difficult and expensive to produce. In order for this known type of artificial airway to be economically viable in view of its cost, it is therefore necessary to produce the device from materials which allow the device to be re-used which further increase the cost of the known device.

The re-use of such devices is in itself inherently inadvisable due not only to the possibility of eventual failure of parts of the device during use but also to the danger of cross-infection between patients if the device is not completely sterilised prior to re-use.

A further disadvantage of the known device is that the complexity of the shape of the mask portion in particular makes it difficult to ensure that the device is effectively sterilised.

Another disadvantage of the known device results from the need for the mask portion thereof to engage in sealing contact with the tissues around the circumference of the patients laryngeal inlet, resulting in the need for the mask portion to be accurately positioned and the risk of this portion of the device being wholly or partially dislodged during movement of a patient during an operation which can cause difficulties in maintaining said sealing contact.

Yet another disadvantage of the known device is that access to the oesophagus is precluded or at least severely restricted by the mask portion of the known device and the relatively large size of the mask portion of the known device only permits oral introduction into the patients hypopharynx and precludes nasal introduction of the device which may be required for certain operations involving for example dental surgery.

OBJECTS AND SUMMARY

The object of the invention is to provide an artificial airway device in which one or more of the above disadvantages of the known device are alleviated.

According to this invention, an artificial airway device to facilitate the ventilation of the lungs of an unconcious patient comprises a hollow elongate member which is open at both ends, an aperture in the wall of the hollow member providing fluid communication between the interior and exterior of said hollow members the aperture being disposed between the ends of said hollow member and sealing means for providing a seal in the patient's pharynx between the external surface of the hollow member and the pharynx on one side of the aperture, between the external surface of the hollow member and the patient's oesophagus on the other side of the aperture and for releasably closing the open end of the hollow member which is inserted into the oesophagus.

Preferably, the sealing means comprises inflatable members adapted when inflated to extend from the external surface of the hollow member for engaging in sealing contact with the patient's pharynx and/or oesophagus.

Preferably, also, the sealing means comprises an upper inflatable member disposed on said one side of the aperture and a lower inflatable member disposed on said other side of the aperture at/or adjacent to the open end of the hollow member.

The lower inflatable member is, preferably, adapted when inflated to extend from the external surface of the hollow member and engage in sealing contact with the patient's oesophagus and distend over the open end of the hollow member which is inserted into the patient's oesophagus to effect closure thereof.

Preferably, each inflatable member is a cuff of extensible material mounted on the external surface of the hollow member.

Preferably, also, each inflatable member is connected to an associated inflation passage through which it is supplied with fluid to effect inflation thereof.

At least part of the or each inflation passage is, preferably, formed in the hollow elongate member as an integral part thereof.

Preferably, the or each inflation passage is connected at the end thereof remote from the associated inflatable member to an associated pilot tube through which fluid is supplied to effect inflation thereof, the other end of the pilot tube extending beyond the external end of the hollow member.

Alternatively, the or each inflation passage may consist of a pilot tube mounted on and/or secured to the external or internal surface of the hollow member.

Preferably, a closeable aperture is provided at or adjacent to the end of the hollow member remote from the end thereof which is inserted into the patient's oesophagus to allow access to the interior of the hollow member.

Preferably, also, the hollow member is a cylindrical tube formed of a flexible material to facilitate insertion thereof into the patient's pharynx either orally or nasally.

BRIEF DESCRIPTION OF THE DRAWINGS

Preferred embodiments of the invention will now be described, by way of example only, with reference to the accompanying drawings of which.

DESCRIPTION

Figure 1:
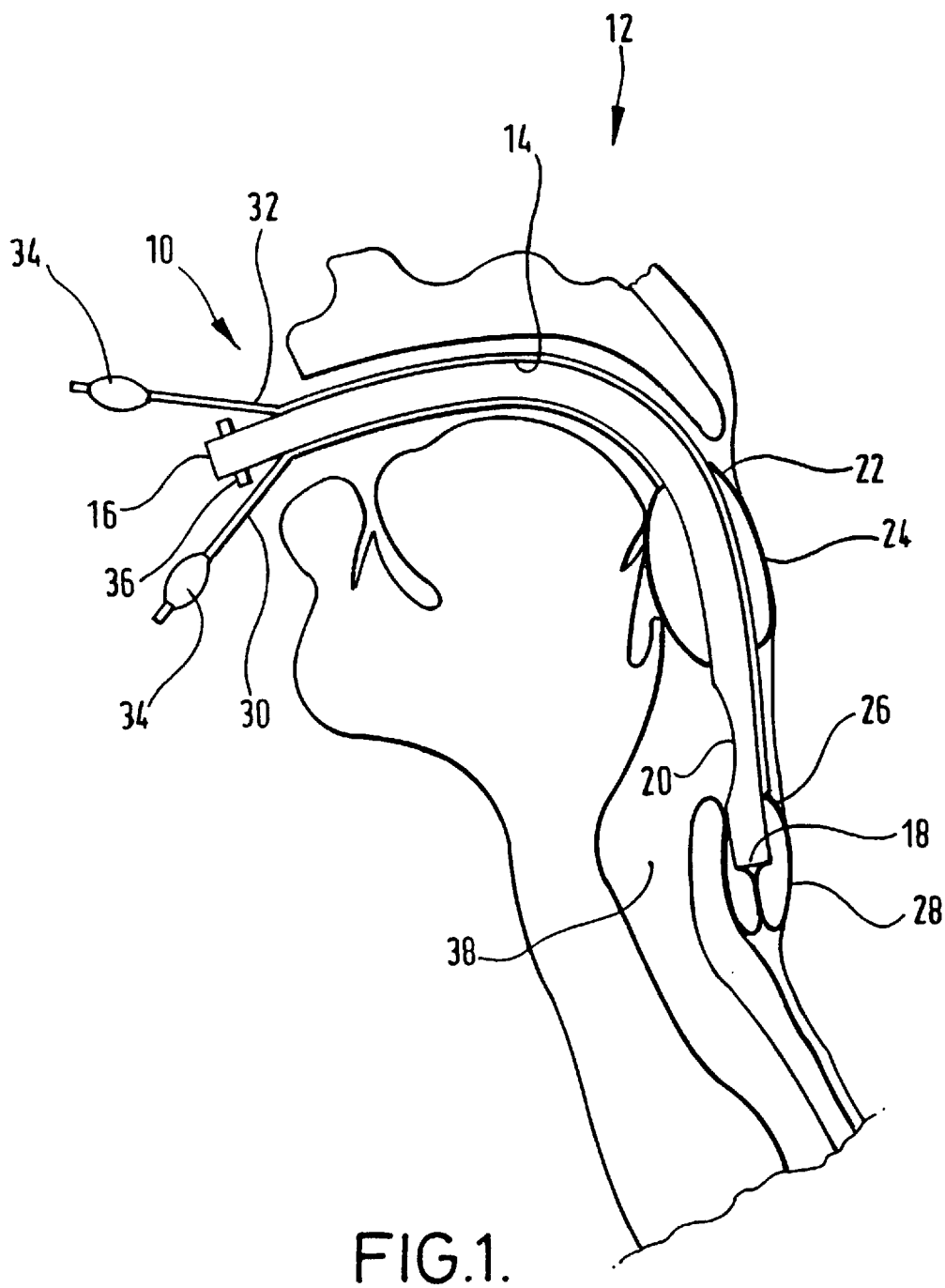
FIG. 1 is a diagrammatic side elevation of an artificial airway device disposed in operative position in a patient.
Figure 2:
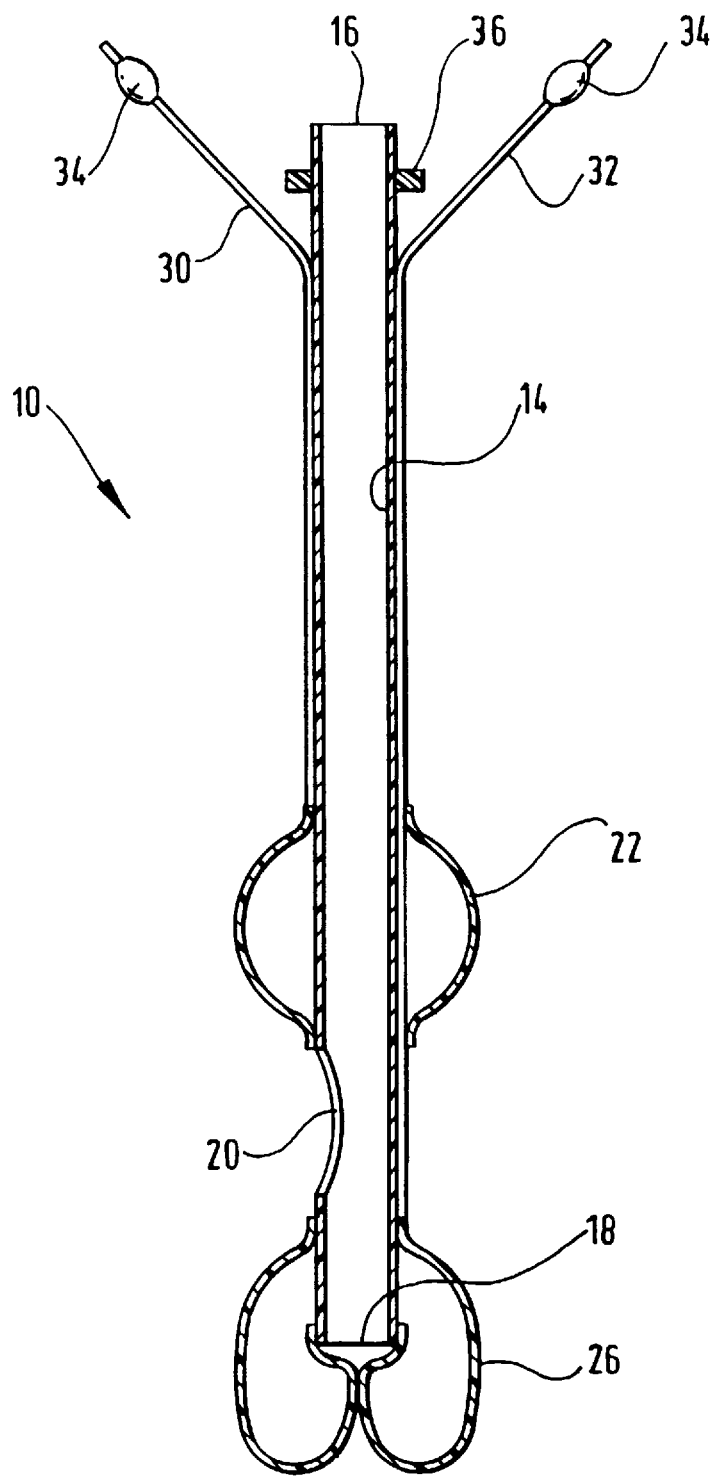
FIG. 2 is a diagrammatic partly sectioned side elevation of the artificial airway device.

Referring now to FIGS. 1 and 2 of the drawings, an artificial airway device indicated generally at 10 for facilitating ventilation of the lungs of an unconcious patent indicated generally at 12 comprises an elongate hollow tube 14 formed of a flexible plastics material. The tube 14 is open at both ends 16 and 18 respectively and an aperture 20 of elliptical shape is formed in the wall of the tube 14 at a point between the ends which is nearer to the internally inserted open end 18 of the tube 14 than to the external open end 16 thereof.

An inflatable tubular cuff 22 of extensible material is mounted on the external surface of the tube 14 at a point between the end 16 thereof and the aperture 20 therein to enable the cuff 22 to form a seal between the external surface of the tube 14 and the patient's oropharynx 24.

An inflatable tubular cuff 26 of extensible material is mounted on the external surface of the tube at the end 18 thereof. The end of the cuff 26 adjacent to the aperture 20 is secured to the external surface of the tube 14 and the other end of the cuff 26 is connected to the external surface of the tube 14 at the extreme end of the tube 14 or is secured to the internal surface of the tube 14 at said extreme end thereof. The cuff 26 forms a seal between the external surface of the tube 14 and the patient's upper oesophageal sphincter 28 and distends over the open end 18 of the tube 14 to effect closure thereof.

The cuff 22 is connected to a pilot tube 30 and the cuff 26 is connected to a pilot tube 32 through which inflation of the cuffs 24 and 26 are respectively and independently effected. The pilot tubes 30 and 32 are mounted on the external surface of the tube 14 and extend therealong to project beyond the end 16 of the tube 14. The free ends of the pilot tubes 30 and 32 are provided with conventional non-return valves 34 and are connected to conventional inflation equipment (not shown) such as a syringe.

The end 16 of the tube 14 is provided with a flange 36 to facilitate the connection of the tube 14 to conventional anaesthesia equipment (not shown) from which conventional mixtures of gases are administered through the tube 14, and out of the aperture 20 into the patient's larynx 38.

The airway device 10, with the cuffs 22 and 26 is inserted either orally as shown in FIG. 1 of the drawings or due to the simple tubular shape thereof can be inserted nasally (not shown). The tube 14 of the airway device 10 is positioned as shown in FIG. 1 of the drawings with the end 18 disposed in the patient's upper oesophageal sphincter 28, the aperture 20 providing communication between the interior of the tube 14 and the patient's larynx 38 and the cuff 22 positioned in the patient's oropharynx 24.

When the cuffs 22 and 26 are inflated seals are formed between the cuff 22 and the oropharynx 24, between the cuff 26 and the upper oesophageal sphincter 28 and the end 18 of the tube 14 is also closed by the cuff 26 distending over said open end 18. Discrete fluid communication is therefore established between the open end 16 of the tube 14 and the patient's larynx 38 to enable ventilation, either spontaneous or controlled, to be effected. Although the end 18 of the tube 14 is closed by the cuff 26 it will be appreciated that a separate drain or suction tube (not shown) can be inserted through the tube 14 and through the distended cuff 26 to enter the oesophagus which can be of advantage in certain types of operation.

In a modification, although the distending of the cuff 26 over the end 18 of the tube 14 effects closure thereof, it is possible to provide an additional internally mounted cuff in the end 18 of the tube 14 as an alternative means of effecting closure thereof.

Figure 3:
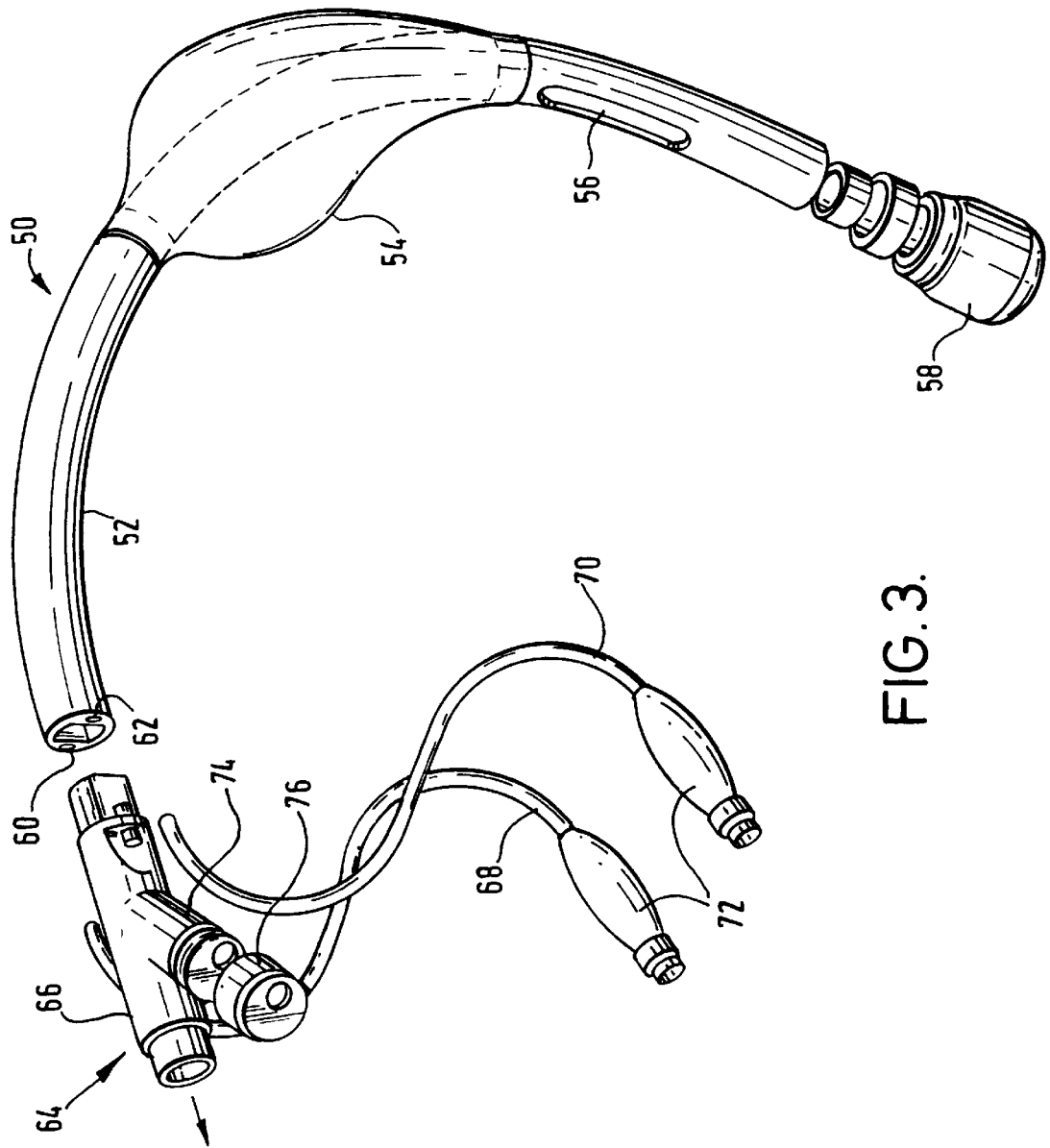
FIG. 3 is a diagrammatic perspective view of an alternative artificial airway device shown in a partly dismantled condition for the sake of clarity.

Referring now to FIG. 3 of the drawings, an alternative artificial airway device indicated generally at 50 facilitates ventilation of the lungs of an unconcious patient and operates in the same manner and is disposed in the same operative position as the device 10 as shown in FIG. 1 of the drawings.

The airway device 50 comprises a tube 52 having an inflatable cuff 54 to form a seal with the oropharynx, an aperture 56 through which gases from the interior of the tube 52 are administered to the larynx and an inflatable cuff assembly 58 providing a seal with the upper oesophageal sphincter and distending over the end of the tube 52 to effect closure thereof. The tube 52 has passages 60 and 62 formed in the wall thereof connected to the cuff 54 and the cuff assembly 58 to enable the cuffs 54 and 58 to be inflated.

A bifurcated end assembly indicated generally at 64 is connected to the end of the tube 52 remote from the cuff assembly 58, the main arm 66 being connectible to the anaesthesia equipment for the administering of gases through the tube 52 and the aperture 56 to the patients larynx. Pilot tubes 68 and 70 are connected via openings in the main arm 66 of the assembly 64 to the passages 60 and 62 and the free ends of the pilot tubes 68 and 70 are provided with non-return valves 72 and are connected to conventional cuff inflation equipment. The branch arm 74 of the assembly 64 communicates with the interior of the main arm 66 and the tube 52 to allow insertion of a drain or suction tube therethrough and through the cuff assembly 58 into the oesophagus. A cap 76 having an aperture therein is rotatable on the end of the branch arm 74 so that said aperture is capable of being brought into alignment with a corresponding aperture in the end of the arm to provide the above communication and rotated to a position where the apertures are out of alignment to effect closure of the branch arm 74.

Although the cuff assembly 58 and the bifurcated end assembly 64 are shown separated from the tube 52 in FIG. 3 for the sake of clarity, it will be appreciated that they are rigidly secured thereto prior to use of the airway device 50.

The simple tubular shapes of the airway devices 10 and 50 not only facilitates nasal insertion where for example dental surgery is to be carried out but also reduces the cost of manufacture of the airway devices 10 and 50 thereby making re-use of the devices unnecessary from a financial standpoint and the relatively simple clean shapes thereof also makes it easier to completely sterilise the devices 10 and 50 if re-use thereof is desired.

What is claimed is:

1. An artificial airway device to facilitate the ventilation of the lungs of an unconcious patient comprising a hollow elongate member which is open at both ends, an aperture in the wall of the hollow member providing fluid communication between the interior and exterior of said hollow member, the aperture being disposed between the ends of said hollow member and sealing means for providing a seal in the patient's pharynx between the external surface of the hollow member and the pharynx on one side of the aperture, between the external surface of the hollow member and the patient's oesophagus on the other side of the aperture and for releasably closing the open end of the hollow member which is inserted into the oesophagus.

2. An artificial airway device according to claim 1, wherein the sealing means comprises inflatable members adapted when inflated to extend from the external surface of the hollow member for engaging in sealing contact with the patient's pharynx and/or oesophagus.

3. An artificial airway device according to claim 2, wherein the sealing means comprises an upper inflatable member disposed on said one side of the aperture and a lower inflatable member disposed on said other side of the aperture at/or adjacent to the open end of the hollow member.

4. An artificial airway device according to claim 3, wherein the lower inflatable member is adapted when inflated to extend from the external surface of the hollow member and engage in sealing contact with the patient's oesophagus and distend over the open end of the hollow member which is inserted into the patient's oesophagus to effect closure thereof.

5. An artificial airway device according to any one of claims 2 to 4, wherein each inflatable member is a cuff of extensible material mounted on the external surface of the hollow member.

6. An artificial airway device according to any one of claims 2 to 4, wherein each inflatable member is connected to an associated inflation passage through which it is supplied with fluid to effect inflation thereof.

7. An artificial airway device according to claim 6, wherein at least part of the or each inflation passage is formed in the hollow elongate member as an integral part thereof.

8. An artificial airway device according to claim 7, wherein the or each inflation passage is connected at the end thereof remote from the associated inflatable member to an associated pilot tube through which fluid is supplied to effect inflation thereof, the other end of the pilot tube extending beyond the external end of the hollow member.

9. An artificial airway device according to any one of claims 2 to 4, wherein the or each inflation passage consists of a pilot tube mounted on and/or secured to the external or internal surface of the hollow member.

10. An artificial airway device according to claim 5, wherein each inflatable member is connected to an associated inflation passage through which it is supplied with fluid to effect inflation thereof.

11. An artificial airway device according to claim 5, wherein the or each inflation passage consists of a pilot tube mounted on and/or secured to the external or internal surface of the hollow member.

12. An artificial airway device according to claim 6, wherein the or each inflation passage consists of a pilot tube mounted on and/or secured to the external or internal surface of the hollow member.

13. An artificial airway device according to claim 5, wherein a closeable aperture is provided at or adjacent to the end of the hollow member remote from the end thereof which is inserted into the patient's oesophagus to allow access to the interior of the hollow member.

14. An artificial airway device according to claim 6, wherein a closeable aperture is provided at or adjacent to the end of the hollow member remote from the end thereof which is inserted into the patient's oesophagus to allow access to the interior of the hollow member.

15. An artificial airway device according to claim 7, wherein a closeable aperture is provided at or adjacent to the end of the hollow member remote from the end thereof which is inserted into the patient's oesophagus to allow access to the interior of the hollow member.

16. An artificial airway device according to claim 8, wherein a closeable aperture is provided at or adjacent to the end of the hollow member remote from the end thereof which is inserted into the patient's oesophagus to allow access to the interior of the hollow member.

17. An artificial airway device according to claim 9, wherein a closeable aperture is provided at or adjacent to the end of the hollow member remote from the end thereof which is inserted into the patient's oesophagus to allow access to the interior of the hollow member.

18. An artificial airway device according to claim 5, wherein the hollow member is a cylindrical tube formed of a flexible material to facilitate insertion thereof into the patient's pharynx either orally or nasally.

19. An artificial airway device according to claim 6, wherein the hollow member is a cylindrical tube formed of a flexible material to facilitate insertion thereof into the patient's pharynx either orally or nasally.

20. An artificial airway device according to claim 7, wherein the hollow member is a cylindrical tube formed of a flexible material to facilitate insertion thereof into the patient's pharynx either orally or nasally.

21. An artificial airway device according to claim 8, wherein the hollow member is a cylindrical tube formed of a flexible material to facilitate insertion thereof into the patient's pharynx either orally or nasally.

22. An artificial airway device according to claim 9, wherein the hollow member is a cylindrical tube formed of a flexible material to facilitate insertion thereof into the patient's pharynx either orally or nasally.

23. An artificial airway device according to any one of claims 1 to 4, wherein a closeable aperture is provided at or adjacent to the end of the hollow member remote from the end thereof which is inserted into the patient's oesophagus to allow access to the interior of the hollow member.

24. An artificial airway device according to any one of claims 1 to 4, wherein the hollow member is a cylindrical tube formed of a flexible material to facilitate insertion thereof into the patient's pharynx either orally or nasally.

25. An artificial airway device according to claim 23, wherein the hollow member is a cylindrical tube formed of a flexible material to facilitate insertion thereof into the patient's pharynx either orally or nasally.

* * * * *